United States Patent [19]

Schoellkopf et al.

[11] Patent Number: 4,958,026
[45] Date of Patent: Sep. 18, 1990

[54] NOVEL DOPAMINE DERIVATIVES, PROCESSES FOR THEIR PREPARATION, AND THEIR USE AS MEDICINAL AGENTS

[75] Inventors: Klaus Schoellkopf; Rudolf Albrecht; Manfred Lehmann; Gertrud Schröeder, all of Berlin, Fed. Rep. of Germany

[73] Assignee: Schering Aktiengesllschaft, Berlin and Bergkamen, Fed. Rep. of Germany

[21] Appl. No.: 867,365
[22] PCT Filed: Aug. 14, 1985
[86] PCT No.: PCT/DE85/00275
   § 371 Date: May 30, 1986
   § 102(e) Date: May 30, 1986
[87] PCT Pub. No.: WO86/01204
   PCT Pub. Date: Feb. 27, 1986

[30] Foreign Application Priority Data

Aug. 15, 1984 [DE] Fed. Rep. of Germany ....... 3430310
Jul. 15, 1985 [DE] Fed. Rep. of Germany ....... 3525563

[51] Int. Cl.$^5$ .................. C07D 231/54; C07D 235/02; C07D 249/18
[52] U.S. Cl. .................................. 548/259; 548/306; 548/332; 548/359
[58] Field of Search ............... 548/126, 259, 305, 306, 548/325, 332, 359, 371; 564/49, 51, 82, 97, 157, 218, 223, 280; 514/359, 361, 394, 403, 405, 406, 597, 605, 616, 629, 646, 866

[56] References Cited

U.S. PATENT DOCUMENTS 4,314,944  2/1982  Huffman ............................ 514/929
4,554,287  11/1985  Stringer et al. ..................... 564/51

FOREIGN PATENT DOCUMENTS 2026402  5/1969  Fed. Rep. of Germany ...... 564/280
1263987  2/1972  United Kingdom ................ 564/280

OTHER PUBLICATIONS

Chem. Abstracts vol. 75(1), Abst. No. 5455k (1971).

Primary Examiner—Mary Lee
Assistant Examiner—M. S. Howard
Attorney, Agent, or Firm—Millen, White & Zelano

[57] ABSTRACT

The disclosure relates to novel dopamine derivatives of general Formula I

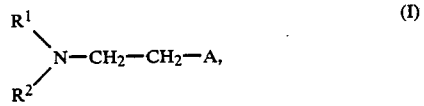 (I)

wherein
A is a substituted phenyl residue of the structure

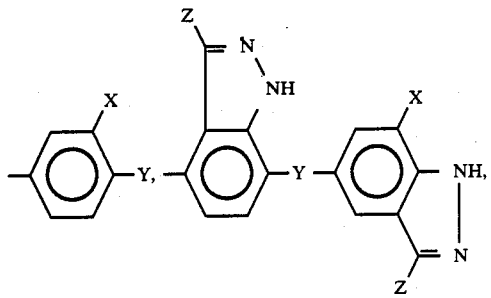

wherein
$R^1$ and $R^2$, being identical or different, mean hydrogen, $C_{1-15}$-alkyl and allyl,
D is

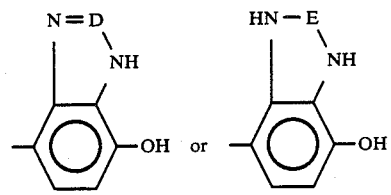

$R_4$ is hydrogen, $C_1$-$C_4$-alkyl, $CF_3$, $NH_2$
E is

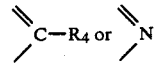

,

—SO$_2$—,
X is OH, NH$_2$,

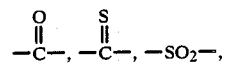

and NH—SO$_2$—CF$_3$, if Y=OH,
Y is OH, NH$_2$,

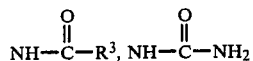

NH—SO$_2$—CF$_3$ and NH—SO$_2$—CH$_3$, if X=OH, but wherein X and Y do not simultaneously mean OH, with $R^3$ being $C_{1-4}$-alkyl, and
Z is H or OH, and, if Z means the hydroxy group, the residue A can also be present in the tautomeric basic form, and their acid addition salts, their preparation, and use as medicinal agents having antihypertensive activity.

5 Claims, No Drawings

NOVEL DOPAMINE DERIVATIVES, PROCESSES FOR THEIR PREPARATION, AND THEIR USE AS MEDICINAL AGENTS

The invention relates to the subject matter of the claims. One aspect of this invention is to provide dopamine derivatives of general Formula I

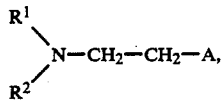

wherein
A represents a substituted phenyl residue of the structure

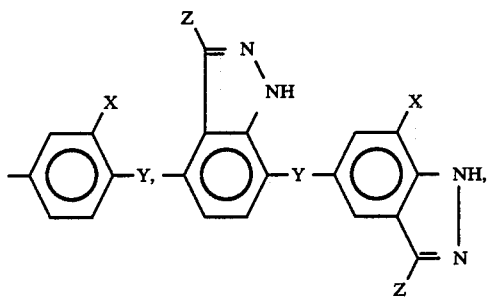

wherein
$R^1$ and $R^2$, being identical or different, mean hydrogen, $C_{1-5}$-alkyl and allyl,
D is

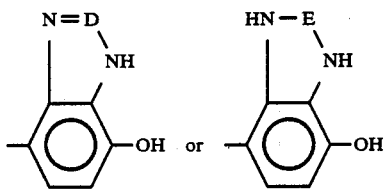

$R_4$ is hydrogen, $C_1-C_4$-alkyl, $CF_3$, $NH_2$

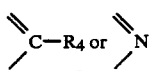

X is OH, $NH_2$,

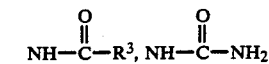

and $NH-SO_2-CF_3$, if $Y=OH$,
Y is OH, $NH_2$,

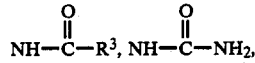

$NH-SO_2-CF_3$ and $NH-SO_2-CH_3$, if $X=OH$, but wherein X and Y do not simultaneously mean OH, with $R^3$ being hydrogen or $C_{1-4}$-alkyl, and
Z is H or OH, and, if Z means the hydroxy group, the residue A can also be present in the tautomeric basic form,
and their acid addition salts, with the proviso that X and Y are not simultaneously OH and $NH-SO_2-CH_3$. In Formula I, $C_{1-4}$-and $C_{1-5}$-alkyl mean lower, straight- or branched-chain alkyl of up to five carbon atoms, such as, for example, methyl, ethyl, isopropyl, pentyl, tertbutyl and 2-methylbutyl.

In case Z in the residue A of Formula I means the hydroxy group, this hydroxy group is part of a tautomeric system.

The following tautomeric system is present wherein both tautomeric, interconvertible forms can be stable.

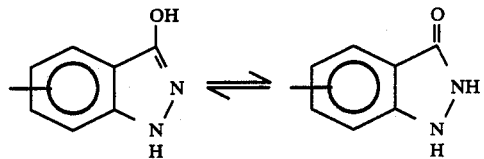

In all benzimidazole and benzotriazole derivatives, two tautomeric forms are possible along the following lines:

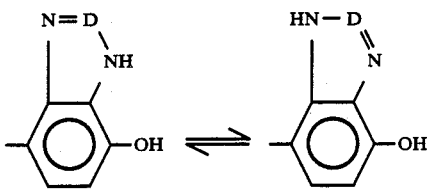

Additionally, compounds wherein $R^4=NH_2$ and $E=$

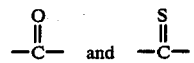

possess tautomerizable structures; the following tautomeric, interconvertible forms can be stable:

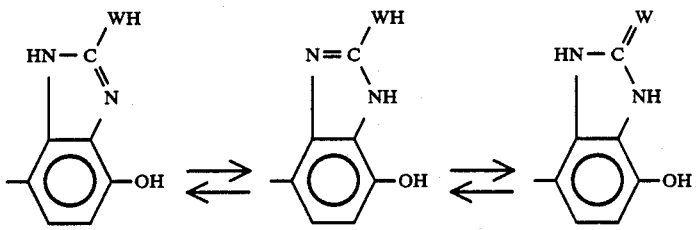

W = O, NH, S

The natural neurotransmitter dopamine affects various biological processes, such as, for example, in the central nervous system where dopaminergic neurons participate in regulating motor coordination and prolactin secretion. Peripherally, dopamine causes various cardiovascular effects, in that it affects arterial tension, evokes a positive inotropic and positive chronotropic effect on the heart, and promotes renal blood flow. These peripheral effects are based, in part, on dopaminergic mechanisms, i.e. those conveyed by dopamine receptors, in part, on other mechanisms, for example adrenergic mechanisms. Dopamine is usable therapeutically only in a limited way on account of this mechanistic nonuniformity, apart from poor bioavailability upon oral administration. Therefore, it would be desirable to provide active agents exhibiting also peripherally effectiveness mechanisms that are entirely or at least in part dopaminergic. Thus, N,N-dipropyldopamine has been developed, for example [Drugs of the Future 7: 469 (1982)], wherein the therapeutically important antihypertensive action appears and is evoked almost exclusively by way of dopaminergic mechanisms. However, one disadvantage displayed by N,N-dipropyl-dopamine is that it has an only very brief duration of activity.

Furthermore, U.S. Pat. Nos. 3,574,741 and 3,758,692 disclose sulfonamidophenylalkylamines, such as 5'-(2-aminoethyl)-2'-hydroxymethanesulfonanilide which exhibits pronounced vasoconstrictive activity.

The literature contains mentions of attempts to obtain compounds having therapeutically usable properties by arylethylamine analogs with benzimidazole or benzotriazole as the aryl portion.

Thus, the following compounds have been described:

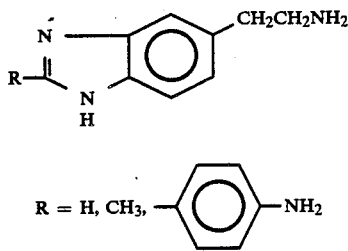

However, these compounds possess hypertensive effects (German Patent No. 294,085).

A similar compound was produced along the same lines with a benzotriazole ring system:

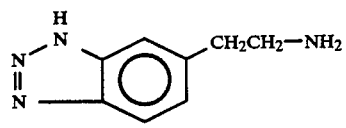

According to data provided by the producers, however, this compound does not display the desired dopaminergic activity [H. Schmidhammer and K. Hohenlohe-Oehringen, Sci. Pharm. 51: 8 (1983)].

It has now been discovered that the dopamine derivatives of Formula I exhibit vasodilatory and antihypertensive activity, the duration of efficacy being substantially prolonged as compared with N,N-dipropyldopamine.

In order to determine the biological efficaciousness of the compounds of this invention, the effect on the blood pressure in dependence on the time was measured on nonanesthetized, spontaneous-hypertensive rats prepared according to the Weeks method.

For this purpose, the compounds were dissolved in distilled water or physiological sodium chloride solution and injected into the vena jugularis. Measuring of the blood pressure took place by way of a chronically implanted catheter in the abdominal aorta. The results are compiled in the table below. The measured values are averaged from tests on respectively 3–6 animals.

TABLE
Lowering of Blood Pressure in Dependence on Time

| Compound | Dose [mg/kg] | Lowering of Blood Pressure[4] | | |
|---|---|---|---|---|
| | | Maximum Effect (%) | After 20 min[3] (%) | After 60 min[3] (%) |
| N,N-Dipropyldopamine, Hydrobromide | 0.3[1] | 15 | 0 | 0 |
| 2-(3-Formylamino-4-hydroxyphenyl)ethylamine | 10[2] | 22 | 15 | 22 |
| N-[4-(2-Aminoethyl)-2-hydroxyphenyl]urea, Hydrochloride | 10[2] | 25 | 13 | 18 |
| N,N-Dipropyl-N-[2-(7-amino-1H-indazol-4-yl)ethyl]amine, Dihydrochloride | 10[2] | 15 | 15 | 8 |

[1]Infused during 20 minutes
[2]Bolus injection
[3]Measured from end of administration
[4]The values indicate reduction of blood pressure in % as compared with the starting value It is known in connection with N,N-dipropyldopamine, selected as the comparison compound, that its effect on blood pressure fades very rapidly [I. Cavero et al., J. Pharmacol. Exp. Ther. 218: 515 (1981)]. Thus, measurements on various rat models have been published from which it can be seen that no activity can be detected any longer 6, 10, 15 or 30 minutes after termination of injection of the compound, depending on model and test method. In the above-cited model of spontaneous-hypertensive rats, lowering of blood pressure, after administering 0.3 mg/kg of N,N-dipropyldopamine, hydrobromide, was less than 1% of the control value as early as 5 minutes after termination of infusion, so that no compound activity could be detected any longer at the subsequent measuring times, i.e. after 20 and 60 minutes.

The second column of the table lists the maximum lowering of blood pressure in % of reduction as compared with the starting value, achieved with the compounds in the indicated dosage at a specific point in time during or after injection of the compound. It can be seen that approximately comparable effects in the range of 15–25% lowering of blood pressure are obtained, for the compounds of this invention, only with very much higher doses as compared with N,N-dipropyldopamine, but these doses are tolerable as regards therapeutic usage in human patients. The decisive aspect, though, is that with these equivalent-effective doses, as compared with N,N-dipropyldopamine, a very much longer-lasting activity is attained so that a marked lowering of blood pressure is observed for the compounds of this invention even after 60 minutes from the end of administration.

The compounds of this invention are thus suitable for antihypertensives. Besides their use as antihypertensives, however, they can also be utilized for improving renal blood flow and for triggering diuretic effect, as well as in the therapy for disturbances of the central nervous system, such as, for example, in Parkinson's disease, schizophrenia, hyperprolactinemia, or as gastric therapeutics, such as, for example, in hyperacidity or stomach ulcers. When using the compound of this invention for increasing renal blood flow, it is possible to administer simultaneously a diuretic to obtain maximum efficacy.

For using the compounds of this invention as medicinal agents, they are made into the form of a pharmaceutical preparation according to conventional methods of galenic pharmacy; these preparations can contain, besides the active ingredient, organic or inorganic, inert excipients especially suitable for enteral administration, such as, for example, water, gelatin, gum arabic, lactose, amylose, magnesium stearate, talc, polyalkylene glycols, etc. The pharmaceutical preparations can be present in solid form, e.g. as tablets, dragees, suppositories, capsules, or in the liquid form, for example as solutions, suspensions or emulsions. They moreover contain optionally auxiliary agents, such as preservatives, stabilizers, wetting agents or emulsifiers, salts for varying osmotic pressure, or buffers.

For use in human patients, the dosage is 50–1,000 mg per day.

The compounds of Formula I according to this invention are produced pursuant to methods known per se.

Thus, it is a process for the preparation of dopamine derivatives of Formula I

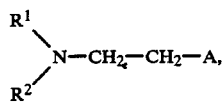
(I)

wherein
A represents a substituted phenyl residue of the structure

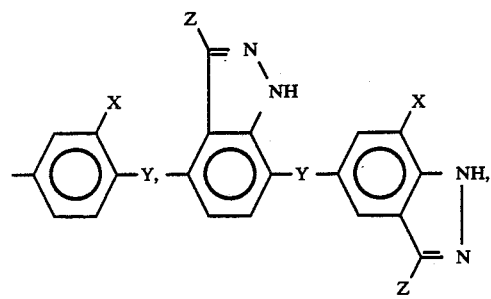

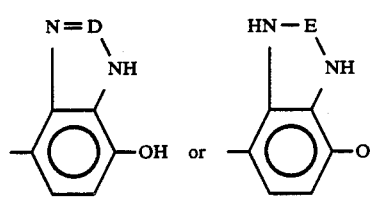

wherein
$R^1$ and $R^2$, being identical or different, mean hydrogen, $C_{1-5}$-alkyl and allyl,
D is

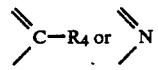

$R_4$ is hydrogen, $C_1$-$C_4$-alkyl, $CF_3$, $NH_2$
E is

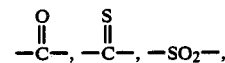

X is OH, $NH_2$,

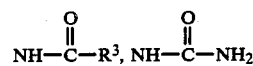

and NH—$SO_2$—$CF_3$, if Y=OH,
Y is OH, $NH_2$,

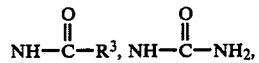

NH—$SO_2$—$CF_3$ and NH—$SO_2$—$CH_3$, if X=OH, but wherein X and Y do not simultaneously mean OH, with $R^3$ being hydrogen or $C_{1-4}$-alkyl, and
Z is H or OH, and their acid addition salts,
characterized by conventionally
(a) subjecting a substituted phenylethylamine of Formula II

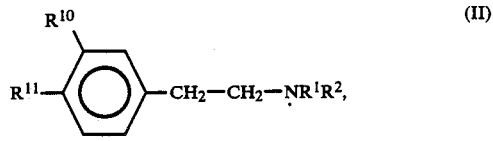
(II)

wherein $R^{10}$ and $R^{11}$ both are, but not simultaneously, the amino and the benzyloxy group, to hydrogenation or ether cleavage, thus obtaining compounds of Formula I wherein X and Y both mean, but not simultaneously, hydroxy and amino;

(b) reacting a substituted phenylethylamine of Formula II with a carboxylic acid chloride $R^3$—COCl, a carboxylic acid anhydride $(R^3$—CO$)_2$O wherein $R^3$ is lower alkyl of 1–4 carbon atoms, trifluoromethanesulfonic acid anhydride, or with sodium cyanate or potassium cyanate, and subsequently splitting off the benzyl group, obtaining compounds of Formula I wherein X and Y both mean, but not simultaneously, hydroxy and acylamido NH—$COR^3$, wherein $R^3$ has the meanings given above, trifluoromethylsulfonamido NH—$SO_2$—$CF_3$ and, respectively, ureido NH—CO—$NH_2$;

(c) in a compound of Formula III

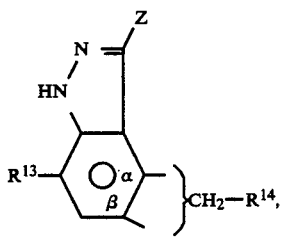 (III)

wherein

Z has the meanings given above, $R^{14}$ stands for $CH_2$—$NR^1R^2$ ($R^1$ and $R^2$ having the above meanings), CN, or $CH_2$—NH—$COCF_3$, and $R^{13}$ is $NO_2$, $NH_2$, or $OCH_3$, the group $CH_2$—$R^{14}$ being able to be in the $\alpha$- or $\beta$-position, (c1) if $R^{13}$ equals $NO_2$, reducing same to the amino group, (c2) if $R^{13}$ equals $NH_2$, hydrolyzing same to the hydroxy group, or (c3) reacting the amino group with a carboxylic acid chloride $R^3COCl$, a carboxylic acid anhydridge ($R^3$—CO)$_2$O wherein $R^3$ has the meanings given above, or with methanesulfonyl chloride, wherein compound of Formula I are obtained with X meaning $R^3CONH$ or $CH_3SO_2NH$, (c4) if $R^{13}$ equals $OCH_3$, subjecting same to an ether cleavage, wherein compounds of Formula I are obtained wherein X means the hydroxy group and, if $R^{14}$ means the grouping $CH_2$—NH—$COCF_3$, $R^1$ and $R^2$ are hydrogen;

(d) reacting a substituted phenylethylamine of Formula IV

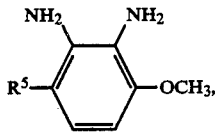 (IV)

wherein $R^5$ is hydrogen or the residue

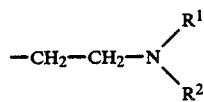

with $R^1$ and $R^2$ having the above-indicated meanings, with a reagent R

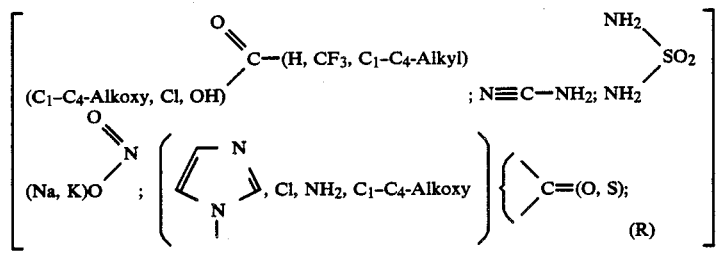

and subjecting to ether cleavage, optionally after introduction of $C_1$-$C_5$-alkyl groups on the N-atom of the aminoethyl side chain, or in case $R^5$=H, after introduction of a formyl group ($R^5$=CHO), conversion into a nitrovinyl group ($R^5$=CH=CH—$NO_2$), reduction to an aminoethyl group ($R^5$=$CH_2$—$CH_2$—$NH_2$) and $C_1$-$C_5$-alkylation at this $CH_2$—$CH_2$—$NH_2$-group.

Hydrogenation of compounds of Formula II in accordance with process version (a) takes place by introducing hydrogen into a solution of II in a customary solvent, such as methanol, ethanol, tetrahydrofuran, acetic acid, etc., in the presence of a noble metal catalyst, such as, for example platinum or palladium, at room temperature and under normal pressure.

Ether cleavage of compounds of Formula II is performed by treatment with hydrogen bromide at room temperature or temperatures up to the boiling point.

The ether cleavage can, however, also be accomplished with other reagents suitable for ether splitting, such as, for example, boron tribromide, trimethylsilyl iodide, ethanethiol in the presence of aluminum chloride, etc.

Derivatization of the amino group according to process version (b) can be effected, besides by means of acid anhydrides or acid halogenides, with all acylating reagents, such as, for example with acid azides, acids in the presence of dicyclohexylcarbodiimide, etc.

Reduction of the nitro group in compounds of Formula III according to process version (c1) can take place by catalytically activated hydrogen, or with zinc in acetic acid, iron in hydrochloric acid, tin(II) chloride, etc.

Hydrolysis of an amino group according to process version (c2) can be performed in sulfuric acid at elevated temperature.

The compounds of Formula I wherein A is a substituted phenyl residue of the structure

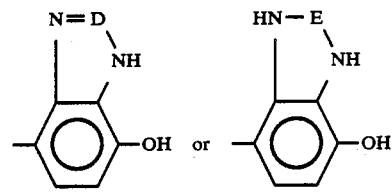

are produced by reacting a substituted phenylethylamine of Formula IV

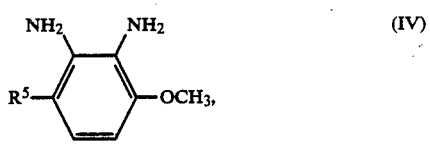 (IV)

wherein $R^5$ is hydrogen or the residue

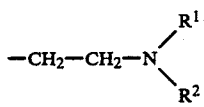

with R¹ and R² having the above-indicated meanings, with a reagent R

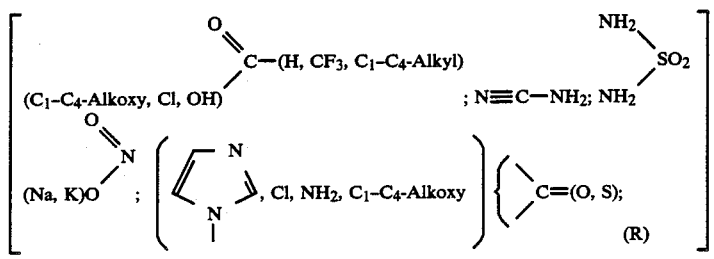

and subjecting to ether cleavage, optionally after introduction of $C_1$–$C_5$-alkyl groups on the N atom of the aminoethyl side chain, or in case $R^5$=H, after introduction of a formyl group ($R^5$=CHO), conversion into a nitrovinyl group (R5=CH=CH—NO₂), reduction to an aminoethyl group ($R^5$=CH₂—CH₂—NH₂), and $C_1$–$C_5$-alkylation at this group CH₂—CH₂—NH₂.

Preparation of the starting compounds IV and their transformation to the compounds of Formula I take place according to conventional methods.

Reaction of the compounds of Formula IV with the corresponding reagent R as the carboxylic acid derivative is preferably conducted at 100°–120° C.

Reaction of the compounds of Formula IV with cyanamide is performed in aqueous mineral acids at temperatures of 80°–120° C.

Reaction of compounds of Formula IV with alkali nitrate is preferably performed in aqueous mineral acids or aqueous carboxylic acids. For example, a compound of Formula IV is dissovled in 30% strength acetic acid and reacted with sodium nitrite at temperatures of −5° to +20° C.

Reaction of compounds of Formula IV with carbonic acid derivatives is preferably effected in inert solvents, such as toluene, lower alcohols, or tetrahydrofuran. For example, a compound of Formula IV is dissolved in tetrahydrofuran and reacted with carbonyl-N,N'-diimidazole or thiocarbonyl-N,N'-diimidazole at temperatures of 40°–65° C.

Reaction of compounds of Formula IV with sulfamide is preferably performed in a high-boiling, inert solvent, such as, for example, diglyme, at temperatures of 80° C. to the boiling temperature of the solvent.

The ether cleavage of the thus-obtained compounds can be conducted according to any of the methods described for this reaction, but, in two preferred versions, takes place by heating with hydrobromic acid at temperatures of 100°–125° C. or with boron tribromide in an inert solvent, such as methylene chloride, at temperatures of 0°–40° C.

The starting compounds required for preparing the compounds of this invention are either known or can be synthesized as follows:

Preparation of the Starting Compounds 2-(4-Benzyloxy-3-nitrophenyl)acetic Acid Dipropylamide Within 10 minutes, 82.5 g of 2-(4-benzyloxy-3-nitrophenyl)acetic acid [J. Med. Chem. 20: 1263 (1977)] is introduced into thionyl chloride heated to 48° C. The mixture is heated to 80° C. for one hour and subsequently concentrated under vacuum. The remaining, crude acid chloride is dissolved in 1.17 l of acetone and, under ice cooling, 78.5 ml of dipropylamine is added. The mixture is stirred for 30 minutes at room temperature. After the crystalline material has been filtered off, the solution is concentrated. Recrystallization from diisopropyl ether yields 65.9 g of 2-(4-benzyloxy-3-nitrophenyl)acetic acid dipropylamide, mp 67°–68° C.

2-(3-Amino-4-benzyloxyphenyl)acetic Acid Dipropylamide

In the presence of Raney nickel, 36.0 g of 2-(4-benzyloxy-3-nitrophenyl)acetic acid dipropylamide is hydrogenated in 600 ml of methanol until 6.7 l of hydrogen has been absorbed, which takes about 4.5 hours. The crude product obtained after removing the catalyst by filtration and after evaporation is chromatographed on silica gel with cyclohexane/ethyl acetate (1:1), thus obtaining 24.4 g of pure 2-(3-amino-4-benzyloxyphenyl)acetic acid dipropylamide as an oil.

2-Benzyloxy-5-(2-dipropylaminoethyl)aniline

A solution of 13.9 g of 2-(3-amino-4-benzyloxyphenyl)acetic acid dipropylamide in 65 ml of tetrahydrofuran is added dropwise under a nitrogen atmosphere into 12 ml of a one-molar solution of borane in tetrahydrofuran, cooled to +5° C., during a period of 20 minutes. Subsequently, the mixture is agitated for 4 hours at room temperature and refluxed for 22 hours. The mixture is combined with semiconcentrated hydrochloric acid and water and the tetrahydrofuran is distilled off. The aqueous solution is then adjusted to a pH value of 10 with sodium hydroxide and extracted by shaking with ether. The ether solution yields, after evaporation and chromatography on silica gel with methylene chloride/acetone (1:1), 8.93 g of pure 2-benzyloxy-5-(2-dipropylaminoethyl)-aniline as an oil. Treatment of this product with 2N HCl in methanol and evaporation yield 2-benzyloxy-5-(2-dipropylaminoethyl)aniline, dihydrochloride, mp 111°–112° C.

4-Benzyloxy-3-nitrobenzaldehyde

At 100° C., 167.0 g of 4-hydroxy-3-nitrobenzaldehyde, 311.0 g of potassium carbonate, and 211.0 g of benzyl chloride are agitated in 2 l of dimethylformamide for 16 hours. The resultant reaction mixture is poured into 10 l of water, the thus-separated solid product is filtered off and recrystallized from ethanol, yielding 215.0 g of 4-benzyloxy-3-nitrobenzaldehyde, mp 100°–102° C.

4-Benzyloxy-3-nitrobenzyl Alcohol

Under ice cooling, 75.7 g of sodium borohydride is introduced within one hour into 128.0 g of 4-benzyloxy-3-nitrobenzaldehyde in 4.2 l of methanol. After 1.5 hours of agitation at room temperature, 1.1 l of 2N HCl is added dropwise. The isolated reaction product is recrystallized from a mixture of 680 ml of diisopropyl ether and 170 ml of isopropanol, thus obtaining 103.0 g of 4-benzyloxy-3-nitrobenzyl alcohol, mp 76°–77° C.

4-Benzyloxy-3-nitrobenzyl Chloride

Under agitation, 58.3 g of 4-benzyloxy-3-nitrobenzyl alcohol is introduced in incremental portions into 250 ml of thionyl chloride, stirred for 30 minutes at room temperature, and concentrated under vacuum. The residue is recrystallized from diisopropyl ether while decolorizing with active carbon, thus producing 50.9 g of 4-benzyloxy-3-nitrobenzyl chloride, mp 60°–61° C.

4-Benzyloxy-3-nitrophenyl)acetonitrile 111.0 g of 4-benzyloxy-3-nitrobenzyl chloride and 21.6 g of sodium cyanide in 800 ml of dimethyl sulfoxide are stirred for 2.5 hours at 40° C., then poured into 1.6 l of ice water. The solid product is recrystallized from ethanol, yielding 95.0 g of (4-benzyloxy-3-nitrophenyl)acetonitrile, mp 91°–97° C.

(3-Amino-4-benzyloxyphenyl)acetonitrile

In the presence of Raney nickel, 53.6 g of (4-benzyloxy-3-nitrophenyl)acetonitrile in 1.2 l of methanol is hydrogenated until 12.2 l of hydrogen has been absorbed. The crude product obtained after removing the catalyst by filtration and after evaporation is purified by chromatography on silica gel with cyclohexane/ethyl acetate (1:1), thus obtaining 36.5 g of (3-amino-4-benzyloxyphenyl)acetonitrile as an oil.

5-(2-Aminoethyl)-2-benzyloxyaniline, Hydrochloride

In the presence of Raney nickel, 9.5 g of (3-amino-4-benzyloxyphenyl)acetonitrile is hydrogenated in 60 ml of ammonia-saturated methanol at 100° C. and under a pressure of 5,000 kPa. The hydrogenation product is chromatographed on silica gel with methylene chloride/methanol (7:3), thus obtaining 6.82 g of 5-(2-aminoethyl)-2-benzyloxyaniline as an oil, converted by treatment with 2N HCl in methanol and evaporation into the hydrochloride.

3-Benzyloxy-4-nitrotoluene 61.2 g of 3-hydroxy-4-nitrotoluene, 66.3 g of potassium carbonate, and 54.7 ml of benzyl chloride are heated in 800 ml of dimethylformamide to 100° C. for 1.5 hours; after cooling, the mixture is poured into water, and the thus-precipitated material is recrystallized from ethanol, yielding 82.0 g of 3-benzyloxy-4-nitrotoluene, mp 49°–51° C.

N-[2-(3-Benzyloxy-4-nitrophenyl)ethenyl]-N,N-dimethylamine 16.0 g of 3-benzyloxy-4-nitrotoluene and 23.0 g of tert-butoxybis(dimethylamino)methane are heated for 8 hours to 100° C. After allowing the mixture to stand for 8 hours at room temperature, the pure reaction product is crystallized. This product is filtered off and washed with a mixture of ethyl acetate and cyclohexane 1:4, thus obtaining 18.7 g of 1-(3-benzyloxy-4-nitrophenyl)-2-dimethylaminoethene, mp 111°–114° C.

(3-Benzyloxy-4-nitrophenyl)acetonitrile 18.7 g of N-[2-(3-benzyloxy-4-nitrophenyl)ethenyl]-N,N-dimethylamine and 21.3 g of hydroxylamineorthosulfonic acid in 420 ml of water are stirred for 3 days at room temperature. The thus-separated solid product is chromatographed on silica gel with cyclohexane/acetic acid (1:1), thus obtaining 7.7 g of (3-benzyloxy-4-nitrophenyl)acetonitrile, mp 73°–85° C.

2-(3-Benzyloxy-4-nitrophenyl)ethylamine, Hydrochloride 2.7 g of (3-benzyloxy-4-nitrophenyl)acetonitrile is reduced with diborane, as described in the preparation of 2-benzyloxy-5-(2-dipropylamino)aniline, and converted into the hydrochloride, thus obtaining 3.2 g of 2-(3-benzyloxy-4-nitrophenyl)ethylamine, hydrochloride.

N-[2-(3-Benzyloxy-4-nitrophenyl)ethyl]-N,N-dipropylamine

Under ice cooling, 2.1 ml of propionaldehyde is added gradually dropwise to 0.92 g of 2-(3-benzyloxy-4-nitrophenyl)ethylamine, hydrochloride, in 20 ml of methanol, and 0.38 g of sodium cyanoborohydride is added thereto after stirring for 15 minutes. The mixture is agitated for 2 hours at 0° C. and for hours at room temperature, then acidified with 2N hydrochloric acid, and the isolated product is chromatographed on silica gel with methylene chloride/acetone (1:1), yielding 610 mg of N-[2-(3-benzyloxy-4-nitrophenyl)ethyl)]-N,N-dipropylamine.

N-[2-(4-Amino-3-benzyloxyphenyl)ethyl]-N,N-dipropylamine 10.9 g of N-[2-(3-benzyloxy-4-nitrophenyl)ethyl]-N,N-dipropylamine is hydrogenated analogously to the production of 2-(3-amino-4-benzyloxyphenyl)acetic acid dipropylamide and the product chromatographed on silica gel with methylene chloride/acetone (1:1), thus obtaining 7.0 g of N-[2-(4-amino-3-benzyloxyphenyl)ethyl]-N,N-dipropylamine as an oil.

2-(4-Amino-3-benzyloxyphenyl)ethylamine, Hydrochloride

In the presence of Raney nickel, 3.2 g of 2-(3-benzyloxy-4-nitrophenyl)ethylamine, hydrochloride, is hydrogenated in 50 ml of methanol, thus producing, after recrystallizing the product from ethanol, 1.36 g of 2-(4-amino-3-benzyloxyphenyl)ethylamine, hydrochloride, mp 181°–184° C.

N,N-Dimethyl-N-[2-(7-nitro-1H-indazol-4-yl)-ethenyl]amine 17.7 g of 4-methyl-7-nitro-1H-indazole [Chem. Ber. 37: 2556 (1904)] and 68.0 g of tertbutoxybis(dimethylamino)methane are heated to 80° C. for 45 minutes, combined with diisopropyl ether, suctioned off, and washed with diisopropyl ether, thus producing 22.0 g of N,N-dimethyl-N-[2-(7-nitro-1H-indazol-4-yl)ethenyl]amine, mp 255° C.

N,N-Dimethyl-N-[2-(7-nitro-1H-indazol-4-yl) ethyl]amine 16.2 g of N,N-dimethyl-N-[2-(7-nitro-1H-indazol-4-yl)ethenyl]amine is dissolved in 200 ml of acetic acid and combined under ice cooling in incremental portions with 6.3 g of sodium cyanoborohydride within 30 minutes. After another 30 minutes, the mixture is combined with ice and ethyl acetate, adjusted to 8–9 with concentrated sodium hydroxide solution, and extracted with ethyl acetate. The solution is dried, concentrated, and the residue recrystallized from ethyl acetate/diisopropyl ether, thus obtaining 13.8 g of N,N-dimethyl-N-[2-(7-nitro-1H-indazol-4-yl)ethyl]amine, mp 145°–146° C.

N,N-Dipropyl-N-[2-(7-nitro-1H-indazol-4-yl) ethenyl]amine 2.1 g of 4-methyl-7-nitro-1H-indazole and 5.0 g of tert-butoxybis(dipropylamino)methane are heated to 80° C. in 10 ml of tetrahydrofuran for 2.5 hours. The mixture is concentrated, distilled with tetrahydrofuran, and recrystallized from dichloromethane/hexane, yielding 3.1 g of N,N-dipropyl-N-[2-(7-nitro-1H-indazol-4-yl)ethenyl]amine, mp 166°–167° C.

N,N-Dipropyl-N-[2-(7-nitro-1H-indazol-4-yl)-ethyl]amine, Hydrochloride 2.9 g of N,N-dipropyl-N-[2-(7-nitro-1H-indazol-4-yl)ethenyl]amine is reduced as described in preparing N,N-dimethyl-N-[2-(7-nitro-1H-indazol-4-yl)ethyl]amine. The product is chromatographed on silica gel with methanol/dichloromethane 1:4 and treated with ethereal hydrochloric acid in methanol. After recrystallization from methanol/diethyl ether, 0.9 g of N,N-dipropyl-N-[2-(7-nitro-1H-indazol-4-yl)ethyl]amine, hydrochloride, is obtained, mp 180.5–182.5° C.

2-(7-Nitro-1H-indazol-4-yl)acetonitrile

At room temperature, 23.3 g of N,N-dimethyl-N-[2-(7-nitro-1H-indazol-4-yl)ethenyl]amine and 35.0 g of hydroxylamine-orthosulfonic acid are agitated in 400 ml of water for 24 hours. The precipitate is suctioned off, washed with water, and recrystallized from ethyl acetate, thus obtaining 16.0 g of 2-(7-nitro-1H-indazol-4-yl)acetonitrile, mp 198°–200° C.

2-Amino-3-methoxy-6-(2-trifluoroacetamidoethyl)benzoic Acid Methyl Ester and 2-Amino-3-methoxy-6-(2-trifluoroacetamidoethyl)benzoic Acid 2.84 g of N-[2-(2,3-Dihydro-2,3-dioxo-7-methoxy-1H-indol-4-yl)ethyl]trifluoroacetamide [J. Med. Chem. 26 : 933 (1983)] is dissolved in 40 ml of methanol, 10 ml of water and 10.8 ml of 1N sodium hydroxide solution, combined within 5 minutes under ice cooling with 13 ml of hydrogen peroxide (3%), and stirred for 30 minutes at room temperature. The mixture is combined with 40 1 of water and extracted once by shaking with ethyl acetate (fraction 1). The aqueous phase is acidified with hydrochloric acid and extracted three times by shaking with ethyl acetate (fraction 2).

Fraction 1 is purified on a silica gel column (system: cyclohexane/ethyl acetate 1:1) and recrystallized from diisopropyl ether/hexane, thus obtaining 1.0 g of 2-amino-3-methoxy-6-(2-trifluoroacetamidoethyl)benzoic acid methyl ester, mp 59°14 60° C. After adding ethereal hydrochloric acid, the hydrochloride is obtained, mp 173-175° C. (decomposition).

Fraction 2 is purified on a silica gel column (system: dichloromethane/methanol 4:1), yielding 1.3 g of 2-amino-3-methoxy-6-(2-trifluoroacetamidoethyl)benzoic acid, mp 169°–171° C. (decomposition).

N-[2-(3-Hydroxy-7-methoxy-1H-indazol-4-yl)ethyl]trifluoroacetamide and N-[2-(2,3-Dihydro-7-methoxy-3-oxo-1H-indazol-4-yl)ethyl]trifluoroacetamide 6.6 g of 2-amino-3-methoxy-6-(2-trifluoroacetamidoethyl)benzoic acid methyl ester is combined with 30 ml of 5N hydrochloric acid and purified at a temperature of −3° C. within 5 minutes with 1.5 g of sodium nitrite in 5 ml of water. The mixture is stirred for 20 minutes at −3° C., cooled to −10° C., and combined with a solution of 12.9 g of tin(II) chloride, dihydrate, in 20 ml of concentrated hydrochloric acid. The mixture is agitated for 2.5 hours at 0° C. and for 0.5 hour at room temperature; the precipitate is dissolved by combining with ethyl acetate, again stirred for 0.5 hour at room temperature, the organic phase is separated, and the aqueous phase is washed twice with ethyl acetate.

The ethyl acetate solutions are concentrated and the residue stirred at room temperature with saturated sodium bicarbonate solution and ethyl acetate for 16 hours. After concentration and recrystallization from methanol/diisopropyl ether, 2.8 g of N-[2-(3-hydroxy-7-methoxy-1H-indazol-4-yl)ethyl]trifluoroacetamide is obtained, decomposition point 213°–217° C.

1.07 g of the free 2-amino-3-methoxy-6-(2-trifluoroacetamidoethyl)benzoic acid is reacted as described above, thus obtaining 0.36 g of N-[2-(3-hydroxy-7-methoxy-1H-indazol-4-yl)ethyl]trifluoroacetamide.

2-(3-Hydroxy-7-methoxy-1H-indazol-4-yl)ethylamine, Hydrochloride, and 2-(2,3-Dihydro-7-methoxy-3-oxo-1H-indazol-4-yl)ethylamine, Hydrochloride 1.8 g of N-[2-(3-hydroxy-7-methoxy-1H-indazol-4-yl)ethyl]trifluoroadetamide is refluxed in 24 ml of ethanol, 6 ml of water, and 6 ml of concentrated hydrochloric acid for 8 hours. After the mixture has been concentrated, it is recrystallized from methanol/diethyl ether, thus obtaining 1.45 g of 2-(3-hydroxy-7-methoxy-1H-indazol-4-yl)ethylamine, hydrochloride, decomposition point 230°–232° C.

N,N-Dipropyl-N-[2-(3-hydroxy-7-methoxy-1H-indazol-4-yl)ethyl]amine, Hydrochloride, and N,N-Dipropyl-N-[2-(2,3-dihydro-7-methoxy-3-oxo-1H-indazol-4-yl ethyl]amine, Hydrochloride 1.45 g of 2-(3-hydroxy-7-methoxy-1H-indazol4-yl)ethylamine, hydrochloride, in 40 ml of methanol is combined with 3.35 ml of propionaldehyde and then, under ice cooling, 688 mg of sodium cyanoborohydride is added in portions; the mixture is stirred for 3 hours at 0° C. and combined with 20 ml of 1N hydrochloric acid. The mixture is further stirred for one hour at room temperature, concentrated under vacuum, the solution is made alkaline with sodium bicarbonate and extracted four times by shaking with ethyl acetate. The combined ethyl acetate phases are dried, concentrated, and chromatographed over a silica gel column (system: toluene/glacial acetic acid/water). The product is treated in methanol with ethereal hdyrochloric acid, thus obtaining 700 mg of N,N-dipropyl-N-[2-(3-hydroxy-7-methoxy-1H-indazol-4-yl)ethyl]amine, hydrochloride, mp 198°–201° C.

N,N-Dimethyl-N-[2-(3-methoxy-4-nitrophenyl)ethenyl]amine 83.5 of 5-methyl-2-nitroanisole and 162.0 g of tert-butoxybis(dimenthylamino)methane is heated for 8 hours to 100° C. After cooling, 111.0 g of N,N-dimenthyl-N-[2-(3-methoxy-4-nitrophenyl)ethenyl]amine is crystallized, mp 57°–58.5° C.

(3-Methoxy-4-nitrophenyl)acetonitrile 19.8 g of N,N-dimethyl-N-[2-(3-methoxy-4nitrophenyl)ethenyl]amine and 30.0 g of hydroxylamineorthosulfonic acid are reacted as described in connection with preparing 2-(7-nitro-1H-indazol-4-yl)acetonitrile, thus obtaining 17.0 g of (3-methoxy-4-nitrophenyl)acetonitrile, mp 85°–86.5° C.

2-(3-Methoxy-4-nitrophenyl)ethylamine

Under ice cooling, 17.0 g of 2-(3-methoxy-4-nitrophenyl)acetonitrile in 50 ml of tetrahydrofuran is combined with 180 ml of 1-molar borane-tetrahydrofuran complex in tetrahydrofuran, stirred for 16 hours at room temperature, and mixed with water. The mixture is agitated at 0° C. for 0.5 hour, 200 ml of 2N hydrochloric acid is added dropwise, and the mixture is again stirred for 2 hours at 0° C. and for 2 hours at room temperature. A pH of 9.5°–10.5 is set with sodium hydroxide solution, and the mixture is extracted four times with ethyl acetate/butanol 10:1. The product is chromatographed on silica gel with methanol/dichloromethane 1:1, thus obtaining 9.0 g of 2-(3-methoxy-4-nitrophenyl)ethylamine as an oil.

Dissolving this product in methanol and mixing with ethereal hydrochloric acid and diethyl ether yields therefrom 2-(w-methoxy-4-nitrophenyl)ethylamine, hydrochloride, mp 149°–151° C. (decomposition).

N-[2-(3-Methoxy-4-nitrophenyl)ethyl]-trifluoroacetamide

At 0° C., 9.7 ml of trifluoroacetic anhydride in 10 ml of dichloromethane is added dropwise to 8.8 g of 2-(3-methoxy-4-nitrophenyl)ethylamine in 200 ml of dichloromethane. After 2 hours at 0° C. and 16 hours at room temperature, the mixture is concentrated and recrystallized from ethyl acetate/hexane, thus obtaining 12.5 g of N-[2-(3-methoxy-4-nitrophenyl)ethyl]trifluoroacetamide, mp 104°–104.5° C.

N-[2-(4-Amino-3-methoxyphenyl)ethyl]trifluoroacetamide

In the presence of 15.0 g of Raney nickel, 12.5 g of N-[2-(3-methoxy-4-nitrophenyl)ethyl]-trifluoroacetamide is hydrogenated in 250 ml of tetrahydrofuran. The product is recrystallized from ethyl acetate/hexane, thus obtaining 10.0 g of N-[2-(4-amino-3-methoxyphenyl)ethyl]trifluoroacetamide, mp 80°–81° C.

Ethyl Ester of 2,3-Dihydro-3-hydroxy-7-methoxy-2-oxo-5-(2-trifluoroacetamidoethyl)-3-indolecarboxylic Acid 2.5 g of N-[2-(4-amino-3-methoxyphenyl)ethyl]trifluoroacetamide and 1.9 ml of mesoxalic acid diethyl ester are dissolved in 25 ml of acetic acid and refluxed for 4 hours. The mixture is concentrated, the residue dissolved in ethyl acetate and extracted twice by shaking with saturated sodium bicarbonate solution. The mixture is concentrated and chromatographed on silica gel with cyclohexane/ethyl acetate 1:1, thus obtaining 2.5 g of 2,3-dihydro-3-hydroxy-7-methoxy-2-oxo-5-(trifluoroacetamidoethyl)-3-indolecarboxylic acid ethyl ester, mp 115°–117° C.

Methyl Ester of 2-Amino-3-methoxy-5-(2-trifluoroacetamidoethyl)benzoic Acid 3.9 g of the ethyl ester of 2,3-dihydro-3-hydroxy-7-methoxy-2-oxo-5-(2-trifluoroacetamidoethyl)-3-indolecarboxylic acid is dissolved in 100 ml of methanol and 20 ml of 1N sodium hydroxide solution and air is passed therethrough for 5 hours. The mixture is combined with 25 ml of 1N hydrochloric acid and extracted by shaking with ethyl acetate. The product is chromatographed over silica gel with cyclohexane/ethyl acetate 1:1 yielding, after recrystallization from ethanol/water, 2.1 g of 2-amino-3-methoxy-5-(2-trifluoroacetamidoethyl)benzoic acid methyl ester, mp 86°–87° C.

N-[2-(3-Hydroxy-7-methoxy-1H-indazol-5-yl)ethyl]trifluoroacetamide and N-[2-(2,3-Dihydro-7-methoxy-3-oxo-1H-indazol-5-yl)ethyl]trifluoroacetamide 2.3 g of 2-amino-3-methoxy-5-(2-trifluoroacetamidoethyl)benzoic acid methyl ester is suspended in 10 ml of 5N hydrochloric acid and reacted as described in the preparation of N-[2-(3-hydroxy-7-methoxy-1H-indazol-4-yl)ethyl]trifluoroacetamide.

The product is 950 mg of N-[2-(3-hydroxy-7-methoxy-1H-indazol-5-yl)ethyl]trifluoroacetamide, decomposition point 232°–233° C.

2-(3-Hydroxy-7-methoxy-1H-indazol-5-yl)ethylamine, Hydrochloride, and 2-(2,3-Dihydro-7-methoxy-3-oxo-1H-indazol-5-yl)ethylamine, Hydrochloride 2.7 g of N-[2-(3-hydroxy-7-methoxy-1H-indazol-5-yl)ethyl]trifluoroacetamide is refluxed with hydrochloric acid as disclosed in the preparation of 2-(3-hydroxy-7-methoxy-1H-indazol-4-yl)ethylamine, hydrochloride, thus obtaining by crystallization from ethanol/diethyl ether 1.5 g of 2-(3-hydroxy-7-methoxy-1H-indazol-5-yl)ethylamine, hydrochloride, decomposition point 266°–268° C.

N,N-Dipropyl-N-[2-(3-hydroxy-7-methoxy-1H-indazol-5-yl)ethyl]amine, Hydrochloride, and N-[2-(2,3-Dihydro-7-methoxy-3-oxo-1H-indazol-5-yl)ethyl]-N,N-dipropylamine, Hydrochloride As described in the preparation of N,N-dipropyl-N-[2-(3-hydroxy-7-methoxy-1H-indazol-4-yl)ethyl]amine, hydrochloride, 2-(3-hydroxy-7-methoxy-1H-indazol-5-yl)ethylamine, hydrochloride, is reacted with propionaldehyde, thus obtaining N,N-dipropyl-N-[2(3-hydroxy-7-methoxy-1H-indazol-5-yl)ethyl]amine, hydrochloride.

N,N-Dimethyl-N-[2-(7-nitro-1H-indazol-5-yl)-ethenyl]amine

5-Methyl-7-nitroindazole [Chem. Ber. 29:306 (1896)] is reacted with tert-butoxybis(dimethylamino)methane as described in the preparation of N,N-dimethyl-N-[2-(7-nitro-1H-indazol-4-yl)ethenyl]amine, thus obtaining N,N-dimethyl-N-[2-(7-nitro-1H-indazol-5-yl)ethenyl]amine.

N,N-Dimethyl-N-[2-(7-nitro-1H-indazol-5-yl)ethyl]amine

N,N-Dimethyl-N-[2-(7-nitro-1H-indazol-5-yl)ethenyl]amine is reacted with sodium cyanoborohydride as set forth in the production of N,N-dimethyl-N-[2-(7-nitro-1H-indazol-4-yl)ethyl]amine, thus obtaining N,N-dimethyl-N-[2-(7-nitro-1H-indazol-5-yl)ethyl]amine.

The following examples are to explain the process of this invention.

Bisdipropylamino-tert-butoxymethane (a) 95 g of N,N-dipropylformamide is added dropwise to 92.1 g of dimethyl sulfate. The mixture is then heated for 3 hours to 75° C. After cooling, extraction is performed with diethyl ether and the residue is dried with a water-jet aspirator at 55° C. Yield : 185 g of N,N-dipropylammonioformic acid methyl ester, methyl sulfate, as an oil.

(b) A solution is prepared from 127.5 g of dipropylamine in 450 ml of toluene. To this solution is added dropwise 185 g of the compound obtained in (a). After 48 hours at room temperature, the mixture is heated for 2.5 hours to 85° C. After cooling, the phases are separated, the product is extracted with diethyl ether and subsequently dried at 55° C. with a water-jet aspirator, thus obtaining 230 g of N,N,N',N'-tetrapropylformamidinium methyl sulfate as an oil.

(c) 230 g of the compound obtained in (b) is thoroughly stirred together with 500 ml of diethyl ether. To this mixture is added in portions 85 g of potassium tert-butylate. Subsequently the mixture is heated under reflux for 2 hours. After cooling, the mixture is filtered off and the residue washed with diethyl ether. After removing the solvent by distillation, the residue is vacuum-distilled, thus producing 26 g of bisdipropylamino-tert-butoxymethane, bp 125° C. at 0.03 mbar.

N-[2-(2,3-Diamino-4-methoxyphenyl)ethyl]-N,N-dimethylamine (a) 57.7 g of 4-methoxy-2,3-dinitrotoluene (J. Chem. Soc. 1927:580) is agitated with 150 ml of bisdimethylamino-tert-butoxymethane [Chem. Ber. 101:41 (1968)] for 6 hours at 80° C. After cooling, the precipitated solid material is filtered off, washed with diisopropyl ether, and dried with a water-jet aspirator, thus producing 54.6 g of β-dimethylamino-4-methoxy-2,3-dinitrostyrene, mp 100°–131° C.

(b) 25 g of the compound obtained in (a) is dissolved in a mixture of 250 ml of methanol, 180 ml of tetrahydrofuran, and 37 ml of glacial acetic acid and cooled to −20° C. To this solution is added in portions 6.3 g of sodium cyanoborohydride. Then the mixture is further stirred for 2 hours at 0° C. After recooling to −20° C., 140 ml of 2N hydrochloric acid is added. Thereafter the mixture is further agitated for one hour at 0° C. The reaction mixture is concentrated and the precipitate is filtered off and recrystallized from methanol, yielding 21.2 g of N-[2-(4-methoxy-2,3-dinitrophenyl)ethyl]-N,N-dimethylamine, hydrochloride, mp 223°–225° C.

(c) 5.7 g of the compound produced in (b) is converted into the free base with sodium bicarbonate solution. This free base is taken up in ethyl acetate and, after adding 4 g of Raney nickel, hydrogenated at room temperature and under normal pressure. After hydrogen absorption has ceased, the catalyst is filtered off and the filtrate concentrated, thus obtaining 3.2 g of N-[2-(2,3-diamino-4-methoxyphenyl)ethyl]-N-N-dimethylamine as an oil.

N-[2-(2,3-Diamino-4-methoxyphenyl)ethyl]N,N-dipropylamine (a) 5.0 g of 4-methoxy-2,3-dinitrotoluene is heated for one hour to 60° C. with 7.5 g of bisdipropylamino-tert-butoxymethane. After cooling, the reaction mixture is freed under high vacuum from volatile components. Yield: 7.1 g of β-dipropylamino-4-methoxy-2,3-dinitrostyrene as an oil.

(b) 6.2 g of the compound obtained in (a) is dissolved in a mixture of 54 ml of methanol, 30 ml of tetrahydrofuran, and 7.5 ml of glacial acetic acid and cooled to −20° C. To this solution is added in portions 0.8 g of sodium cyanoborohydride. Subsequently the mixture is stirred for 2 hours at 20° C. To this solution is then added 30 ml of 2N hydrochloric acid and the mixture agitated for one hour. Thereupon the reaction mixture is concentrated and taken up in sodium bicarbonate solution. The aqueous phase is repeatedly extracted with diethyl ether. The ether phase is separated, dried with sodium sulfate and combined with oxalic acid. The precipitate is filtered off and washed with diethyl ether. Subsequently, the base is liberated with sodium bicarbonate solution and extracted with diethyl ether. After removal of the solvent, 1.2 g of N-[2-(4-methoxy-2,3-dinitrophenyl)ethyl]-N,N-dipropylamine is obtained as an oil.

(c) 0.7 g of the compound produced in (b) is dissolved in 100 ml of ethyl acetate and hydrogenated after adding 1 g of Raney nickel. After hydrogen absorption has ceased, the catalyst is filtered off and the filtrate concentrated, thus obtaining 0.53 g of N-[2-(2,3-diamino-4-methoxyphenyl)ethyl]-N,N-dipropylamine as an oil.

EXAMPLE 1

N-[2-(3-Amino-4-hydroxyphenyl)ethyl]-N,N-dipropylamine, Dihydrochloride 1.9 g of 2-(benzyloxy-5-(2-dipropylaminoethyl)aniline, dihydrochloride, is hydrogenated in 30 ml of methanol in the presence of 150 mg of palladium/carbon (10% strength). After removing the catalyst by filtration, the mixture is concentrated and recrystallized from isopropanol, thus obtaining 0.88 g of N-[2-(3-amino-4-hydroxyphenyl)ethyl]-N,N-dipropylamine, dihydrochloride, mp 127°–151° C.

EXAMPLE 2

N-[2-Hydroxy-5-(2-dipropylaminoethyl)phenyl]formamide (a) Under ice cooling, 4 ml of a mixture of formic acid and acetic anhydride (ratio 3:5) is added dropwise to 3.2 g of 2-(benzyloxy-5-(2-dipropylaminoethyl)aniline in 10 ml of chloroform, then the mixture is stirred for 2 hours at room temperature. The solution is washed with aqueous NaHCO₃ solution, concentrated, and the residue chromatographed on silica gel with methylene chloride/acetone (1:1), yielding 1.8 g of N-[2-benzyloxy-5-(2-dipropylaminoethyl)phenyl]formamide as an oil.

(b) 650 mg of the compound obtained in (a) in 10 ml of methanol is hydrogenated in the presence of 100 mg of palladium/carbon. The solution is filtered, concentrated, yielding 380 mg of pure N-[2-hydroxy-5-(2-dipropylaminoethyl)phenyl]formamide as a vitreous mass.

EXAMPLE 3

N-[5-(2-Dipropylaminoethyl)-2-hydroxyphenyl]urea, Hydrochloride (a) 1.6 g of 2-benzyloxy-5-(2-dipropylaminoethyl)amine in 5 ml of acetic acid and 1.5 ml of water are combined with 0.65 g of sodium cyanate in 5 ml of water. After 2 hours of agitation at room temperature, the reaction mixture is extracted by shaking with methylene chloride. The methylene chloride solution is washed with sodium bicarbonate solution and water, dried, and evaporated, yielding 1.74 of 1-[2-benzyloxy-5-(2-dipropylaminoethyl)phenyl]urea as an oil; this oil crystallizes after standing for some time and exhibits a melting point of 70°–88° C.

(b) 1.7 g of the product prepared according to (a) is hydrogenated in 20 ml of methanol in the presence of 150 mg of palladium-carbon; after removing the catalyst by filtration, 2.3 ml of 2N HCl is added, the mixture is evaporated and the residue recrystallized from isopropanol, thus obtaining 0.85 g of N-[5-(2-dipropylaminoethyl)-2-hydroxyphenyl]urea, hydrochloride, mp 168°–171° C. cl EXAMPLE 4

5-(2-Aminoethyl)-2-hydroxyaniline, Hydrochloride

In the presence of 100 mg of palladiumcarbon, 2.6 g of 5-(2-aminoethyl)-2-benzyloxyaniline, hydrochloride, is hydrogenated in 20 ml of methanol; after recrystallization from ethanol, 0.52 g of 5-(2-aminoethyl)-2-hydroxyaniline, hydrochloride, is obtained, mp 159°–164° C.

EXAMPLE 5

2-(3-Formylamino-4-hydroxyphenyl)ethylamine (a) 2.7 g of 5-(2-aminoethyl)-2-benzyloxyaniline, hydrochloride, in 160 ml of chloroform is combined with 4 ml of a mixture of formic acid and acetic anhydride (3:5). After 5 minutes of agitation at room temperature, a small amount of water is added and the mixture completely evaporated. The residue is chromatographed on silica gel with methylene chloride/methanol 8:2. The thus-purified material is washed in methylene chloride with sodium bicarbonate solution. After evaporation, 1.5 g of 2-(4-benzyloxy-3-formylaminophenyl)ethylamine is obtained as a noncrystalline material.

(b) 1.5 g of the product prepared according to (a) is hydrogenated in 50 ml of methanol in the presence of 100 mg of palladium-carbon, thus obtaining, after recrystallization from ethanol, 160 mg of 2-(3-formylamino-4-hydroxyphenyl)ethylamine, mp 207°–215° C.

EXAMPLE 6

N-[5-(2-Aminoethyl)-2-hydroxyphenyl]urea, Hydrochloride (a) 2.4 g of 5-(2-aminoethyl)-2-benzyloxyaniline, hydrochloride, is dissolved in a mixture of 20 ml of acetic acid, 5 ml of water and 0.5 ml of 2N hydrochloric acid. A solution of 0.72 g of sodium cyanate in 5 ml of water is added and the mixture is stirred for one hour at room temperature. Thereafter, the mixture is diluted with 100 ml of water, the product is extracted by shaking with methylene chloride and recrystallized from isopropanol, thus obtaining 0.56 g of N-[5-(2-aminoethyl)-2-benzyloxyphenyl]urea, mp 176°–180° C.

(b) 0.53 g of the product obtained in (a) is hydrogenated analogously to Example 3(b) and converted into the hydrochloride, thus obtaining 0.40 g of N-[5-(2-aminoethyl)-2-hydroxyphenyl]urea, hydrochloride, as a noncrystalline material

EXAMPLE 7

4-(2-Dipropylaminoethyl)-2-hydroxyaniline, Dihydrochloride

In the presence of 0.1 g of palladiumcarbon, 0.51 g of N-[2-(4-amino-3-benzyloxyphenyl)ethyl]-N,N-dipropylamine is hydrogenated in 10 ml of methanol. The product is chromatographed on silica gel with methylene chloride/methanol/water (65:40:10) and converted into the dihydrochloride by treatment with 2N hydrochloric acid in methanol, yielding 190 mg of 4-(2-dipropylaminoethyl)-2-hydroxyaniline, dihydrochloride.

EXAMPLE 8

N-[2-Hydroxy-4-(2-dipropylaminoethyl)phenyl]formamide (a) As described in Example 2(a), 2.0 g of N-[2-(4-amino-3-benzyloxyphenyl)ethyl]-N,N-dipropylamine is formylated, thus obtaining 2.0 g of N-[2-benzyloxy-4-(2-dipropylaminoethyl)phenyl]formamide as an oil.

(b) 2.0 g of the product described in (a) is hydrogenated as described in Example 2(b), yielding 1.5 g of N-[2-hydroxy-4-(2-dipropylaminoethyl)phenyl]formamide as an oil.

EXAMPLE 9

N-[4-(2-Dipropylaminoethyl)-2-hydroxyphenyl]butyramide, Hydrochloride (a) 0.3 ml of triethylamine is added to 0.65 g of N-[2-(4-amino-3-benzyloxyphenyl)ethyl]-N,N-dipropylamine in 10 ml of tetrahydrofuran, and then 0.23 ml of butyryl chloride is added dropwise thereto. The reaction mixture is stirred for one hour at room temperature, diluted with water, and the product extracted by shaking with methylene chloride, isolating 770 mg of N-[2-benzyloxy-4-(2-dipropylaminoethyl)phenyl]butyramide as an oil from the methylene chloride solution.

(b) 0.77 g of the product described in (a) is hydrogenated analogously to Example 3(b) and converted into the hydrochloride, thus obtaining 0.39 g of N-[4-(2-dipropylaminoethyl)-2-hydroxyphenyl]butyramide, hydrochloride, as an oil.

EXAMPLE 10

N-[4-(2-Dipropylaminoethyl)-2-hydroxyphenyl]trifluoromethanesulfonic Acid Amide (a) Under ice cooling, 0.18 ml of trifluoromethanesulfonic acid anhydride is added dropwise to 0.66 g of N-[2-(4-amino-3-benzyloxyphenyl)ethyl]-N,N-dipropylamine and 0.15 ml of triethylamine in 5 ml of acetone. Thereafter the mixture is stirred for 2 hours at room temperature, concentrated, shaken with water and methylene chloride, and the product obtained after concentrating the methylene chloride solution is chromatographed on silica gel with acetic acid/toluene/water (10:10:1). The purified product is recrystallized from methylene chloride, thus obtaining 0.19 g of N-[2-benzyloxy-4-(2-dipropylaminoethyl)phenyl]trifluoromethanesulfonic acid amide, mp 194°–197° C.

(b) 0.14 g of the product described in (a) is hydrogenated analogously to Example 2(b), obtaining, after recrystallization of the product from methanol, mg of N-[4-(2-dipropylaminoethyl)-2-hydroxyphenyl]trifluoromethanesulfonic acid amide, mp 198°-207° C.

EXAMPLE 11

4-(2-Aminoethyl)-2-hydroxyaniline, Hydrochloride 0.54 g of 2-(4-amino-3-benzyloxyphenyl)ethylamine, hydrochloride, is hydrogenated analogously to Example 4, yielding 0.32 g of noncrystalline 4-(2-aminoethyl)-2-hydroxyaniline, hydrochloride.

EXAMPLE 12

N-[4-(2-Aminoethyl)-2-hydroxyphenyl]formamide (a) 1.4 g of 2-(4-amino-3-benzyloxyphenyl)ethylamine,hydrochloride, is formylated analogously to Example 5(a), thus obtaining 1.1 g of N-[4-(2-aminoethyl)-2-benzyloxyphenyl]formamide as an oil.

(b) 0.43 g of the product set forth in (a) is hydrogenated analogously to Example 5(b); the product is chromatographed on silica gel with dioxane/concentrated ammonia/water (80:20:10), yielding 0.25 g of N-[4-(2-aminoethyl)-2-hydroxyphenyl]formamide.

EXAMPLE 13

N,N-Dimethyl-N-[2-(7-amino-1H-indazol-4-yl)ethyl]amine, Dihydrochloride

In the presence of 1.0 g of Raney nickel, 1.2 g of N,N-dimethyl-N-[2-(7-nitro-1H-indazol-4-yl)ethyl]amine is hydrogenated in 60 ml of tetrahydrofuran. The mixture is filtered, concentrated and recrystallized from ethyl acetate/hexane, thus producing 860 mg of N,N-dimethyl-N-[2-(7-amino-1H-indazol-4-yl)ethyl]amine, mp 125° C. This product is treated, in the amount of 460 mg, with ethanol and ethereal hydrochloric acid, recrystallization from methanol/diethyl ether yielding 505 mg of N,N-dimethyl-N-[2-(7-amino-1H-indazol-4-yl)ethyl]amine, dihydrochloride, mp 231°-232° C.

EXAMPLE 14

N,N-Dimethyl-N-[2-(7-hydroxy-1H-indazol-4-yl)ethyl]amine, Hydrochloride

In an autoclave, 1.2 g of N,N-dimethyl-N-[2-(7-amino-1H-indazol-4-yl)ethyl]amine and 24 ml of 1N sulfuric acid are heated under argon for 16 hours to 180° C. Subsequently the mixture is combined under ice cooling with sodium bicarbonate and extracted by shaking with ethyl acetate/butanol (10:1). The organic phase is dried, concentrated, and the residue is triturated with ethyl acetate, thus obtaining 700 mg of N,N-dimethyl-N-[2-(7-hydroxy-1H-indazol-4-yl)ethyl]amine, mp 233°-234° C., yielding after treatment with methanol and ethereal hydrochloric acid, and recrystallization from methanol/diethyl ether, 680 mg of N,N-dimethyl-N-[2-(7-hydroxy-1H-indazol-4-yl)ethyl]amine, hydrochloride, mp 223°-227° C.

EXAMPLE 15

N-[4-(2-Dimethylaminoethyl)-1H-indazol-7-yl]formamide, Hydrochloride 10 ml of formic acid and 0.9 ,1 of acetic anhydride are refluxed for 15 minutes and combined at room temperature with 1.2 g of N,N-dimethyl-N-[2-(7-amino-1H-indazol-4-yl)ethyl]amine. After 16 hours at room temperature, the mixture is concentrated, combined with saturated sodium bicarbonate solution, and extracted three times with butanol/ethyl acetate (1:5). The product is chromatographed on silica gel with methanol/dichloromethane 1:1, mixed with ethereal hydrochloric acid, and recrystallized from methanol/diethyl ether, thus obtaining 950 mg of N-[4-(2-dimethylaminoethyl)-1H-indazol-7-yl]formamide, hydrochloride, mp 210°-211° C.

EXAMPLE 16

N-[4-(2-Dimethylaminoethyl)-1H-indazol-7-yl]acetamide, Hydrochloride 306 mg of N,N-dimethyl-N-[2-(7-amino-1H-indazol-4-yl -ethyl]amine in 4 ml of acetic acid is stirred for 16 hours with 0.18 ml of acetic anhydride. The product is chromatographed on silica gel with methanol/dichloromethane 1:1 and converted into the hydrochloride with ethereal hydrochloric acid, thus obtaining 180 mg of N-[4-(2-dimethylaminoethyl)-1H-indazol-7-yl]acetamide, hydrochloride, mp 223° C. (from methanol/diethyl ether).

EXAMPLE 17

N-[4-(2-Dimethylaminoethyl)-1H-indazol-7-yl]methanesulfonamide, Hydrochloride

At 0° C., 1.2 g of N,N-dimethyl-N-[2-(7-amino-1H-indazol-4-yl)ethyl]amine in 10 ml of dimethylformamide and 5 ml of tetrahydrofuran is combined with 0.91 ml of methanesulfonyl chloride The mixture is agitated for 2 hours at 0° C. and for 14 hours at room temperature. The product is chromatographed on silica gel with methanol/dichloromethane 1:1 and treated with ethereal hydrochloric acid, obtaining, after recrystallization from methanol/diethyl ether, 550 mg of N-[4-(2-dimethylamino-ethyl)-1H-indazol-7-yl]methanesulfonamide, hydrochloride, mp 203°-205° C.

EXAMPLE 18

N,N-Dipropyl-N-[2-(7-amino-1H-indazol-4-yl)ethyl]amine, Dihydrochloride 600 mg of N,N-dipropyl-N- 2-(7-nitro-1H-indazol-4-yl)ethyl amine, hydrochloride, in 10 ml of methanol and 10 ml of tetrahydrofuran is hydrogenated in the presence of 0.5 g of Raney nickel. The mixture is filtered off from the catalyst, combined with ethereal hydrochloric acid, and concentrated. The residue is recrystallized from methanol/diethyl ether, yielding 360 mg of N,N-dipropyl-N- 2-(7-amino-1H-indazol-4-yl)ethyl amine, dihydrochloride, mp 214°-218° C.

EXAMPLE 19

N,N-Dipropyl-N-[2-(7-hydroxy-1H-indazol4-yl)ethyl]amine, Dihydrochloride (a) 20.2 g of 2-(7-nitro-1H-indazol-4-yl)-acetonitrile in 750 ml of tetrahydrofuran is hydrogenated in the presence of 20.0 g of Raney nickel. The product is recrystallized from tetrahydrofuran/hexane, yielding 15.1 g of 2-(7-amino-1H-indazol-4-yl)acetonitrile, mp 164°-165° C.

(b) 3.44 g of the product described in (a) and 80 ml of 1N sulfuric acid are heated under argon in an autoclave to 170° C for 20 hours. The crystallized product is suctioned off and washed with water, obtaining 3.4 g of 2-(7-hydroxy-1H-indazol-4-yl)acetic acid, mp 258°-260° C. (decomposition).

(c) At −10° C., 2.3 g of the product set forth in (b) in 10 ml of dimethylformamide and 15 ml of tetrahydrofuran is combined with 1.56 ml of N-ethylmorpholine and 1.68 ml of isobutyl chloroformate, then 2.46 ml of dipropylamine in 20 ml of tetrahydrofuran is added after 5 minutes. The mixture is stirred at 0° C. for 0.5 hour and at room temperature for 16 hours, concentrated, and taken up with ethyl acetate and water. From the ethyl acetate solution, after recrystallization from the same solvent, 2.1 g of 2-(7-hydroxy-1H-indazol-4-yl)acetic acid dipropylamide is obtained, mp 164°-165° C.

(d) Under ice cooling, 1.66 g of 2-(7-hydroxy-1H-indazol-4-yl)acetic acid dipropylamide in 150 ml of tetrahydrofuran is combined with 1.5 g of lithium aluminum hydride and stirred for 5 hours at room temperature. The mixture is gently combined with water under ice cooling, and ethyl acetate/saturated sodium bicarbonate solution is added thereto. The product obtained from the ethyl acetate solution is chromatographed on silica gel with toluene/acetic acid/water 10:10:1 and treated with ethereal hydrochloric acid in ethanol, thus obtaining 1.8 g of N,N-dipropyl-N-[2-(7-hydroxy-1H-indazol-4-yl)ethyl]amine, dihydrochloride, mp 125°-127° C.

EXAMPLE 20

N,N-Diallyl-N-[2-(7-hydroxy-1H-indazol4-yl)ethyl]amine, Dihydrochloride (a) 2-(7-Hydroxy-1H-indazol-4-yl)acetic acid is reacted with diallylamine as described in Example 19(c), thus producing 2-(7-hydroxy-1H-indazol4-yl)acetic acid diallylamide, mp 107°-108° C.

(b) The product obtained in (a) is reacted as described in Example 19(d) with lithium aluminum hydride, yielding N,N-diallyl-N-[2-(7-hydroxy-1H-indazol-4-yl)ethyl]amine, hydrochloride, mp 213° C.

EXAMPLE 21

N-[2-(7-Hydroxy-1H-indazol-4-yl)ethyl]amine, Hydrochloride (a) 2.3 g of 2-(7-hydroxy-1H-indazol-4-yl)acetic acid is reacted analogously to Example 19(c) with benzylamine in place of dipropylamine. The product is recrystallized from methanol/diisopropyl ether, thus obtaining 2.6 g of 2-(7-hydroxy-1H-indazol-4-yl)acetic acid benzylamide, mp 188°-190° C.

(b) 2.2 g of 2-(7-hydroxy-1H-indazol-4-yl)acetic acid benzylamide in 60 ml of tetrahydrofuran is introduced dropwise under argon into 1.9 g of lithium aluminum hydride in 50 ml of tetrahydrofuran and refluxed for 16 hours. Subsequently the reaction mixture is worked up as disclosed in Example 19(d). The product is chromatographed on silica gel with methanol/chloroform 1:1, treated with ethereal hydrochloric acid, and recrystallized from methanol/diethyl ether, yielding 1.2 g of N-benzyl-N-[2-(7-hydroxy-1H-indazol-4-yl)ethyl]amine, hydrochloride, mp 163°-165° C. (decomposition).

(c) In the presence of 1.0 g of palladiumcarbon, 870 mg of N-benzyl-N-[2-(7-hydroxy-1H-indazol-4-yl)ethyl]amine, hydrochloride, is hydrogenated in 50 ml of methanol. The product is recrystallized from ethanol/diethyl ether, thus obtaining 565 mg of N-[2-(7-hydroxy-1H-indazol-4-yl)ethyl]amine, hydrochloride, mp 257°-260° C.

EXAMPLE 22

2-(7-Amino-1H-indazol-4-yl)ethylamine, Dihydrochloride

Under 1,000 kPa, 344 mg of 2-(7-amino-1H-indazol-4-yl) acetonitrile in 10 ml of acetic anhydride is hydrogenated in the presence of 0.5 g of Raney nickel at room temperature. The reaction product is chromatographed on silica gel with methanol/dichloromethane, thus isolating N-[2-(7-acetamino-1H-indazol-4-yl)ethyl]acetamide (340 mg, mp 211°-212° C.) which is refluxed in 2 ml of acetic acid and 5 ml of hydrochloric acid for 5 hours, concentrated, and the residue recrystallized from ethanol. Yield: 220 mg of 2-(7-amino-1H-indazol-4-yl)ethylamine, dihydrochloride, mp 288°-291° C. (decomposition).

EXAMPLE 23

N-[4-(2-Aminoethyl)-1H-indazol-7-yl]methanesulfonamide, Hydrochloride (a) At 0° C., 1.7 g of 2-(7-amino-1H-indazol-4-yl)acetonitrile in 15 ml of dimethylformamide and 5 ml of tetrahydrofuran is combined with 0.96 ml of methanesulfonyl chloride and 1.56 ml of N-ethylmorpholine and agitated for 16 hours at room temperature. The mixture is concentrated, chromatographed over silica gel with methanol/dichloromethane (1:3), and recrystallized from methanol, thus producing 2.2 g of N-(4-cyanomethyl-1H-indazol-7-yl)methanesulfonamide, mp 223°-225° C.

(b) 1.4 g of N-(4-cyanomethyl-1H-indazol-7-yl)methanesulfonamide in 60 ml of ethanolic ammonia solution is hydrogenated in the presence of 2.0 g of Raney nickel at 80° C. and under 8,000 kPa within 6 hours. The mixture is filtered off from the catalyst, concentrated, chromatographed over a silica gel column (eluent: methanol/dichloromethane 1:1), combined with ethereal hydrochloric acid, and recrystallized from methanol/diethyl ether, yielding 500 mg of N-[4-(2-aminoethyl)-1H-indazol-7-yl]methanesulfonamide, hydrochloride, mp 120° C. (decomposition).

EXAMPLE 24

N-[2-(3,7-Dihydroxy-1H-indazol-4-yl)ethyl]-N,N-dipropylamine, Hydrobromide,and

N-[2-(2,3-Dihydro-7-hydroxy-3-oxo-1H-indazol-4-yl)ethyl]-N,N-dipropylamine, Hydrobromide Under argon, 480 mg of N,N-dipropyl-N-[2-(3-hydroxy-7-methoxy-1H-indazol-4-yl)ethyl]amine, hydrochloride, is heated to 120° C. in 5 ml of aqueous hydrogen bromide (65%) for 4 hours. The mixture is concentrated and once distilled with water. The residue is dried, triturated with diethyl ether, and repeatedly recrystallized from ethanol/acetone/diethyl ether, thus obtaining 340 mg of N-[2-(3,7-dihydroxy-1H-indazol-4-yl)ethyl]-N,N-dipropylamine, hydrobromide, decomposition point 242°-244° C.

EXAMPLE 25

2-(3,7-Dihydroxy-1H-indazol-4-yl)ethylamine, Hydrobromide, and 2-(2,3-dihydro-7-hydroxy-3-oxo-1H-indazol-4-yl)ethylamine, Hydrobromide Under argon, 750 mg of N-[2-(3-hydroxy-7-methoxy-1H-indazol-4-yl]trifluoroacetamide is heated to 120° C. with 5 ml of aqueous hydrogen bromide (65%) for 2 hours. The crystallized product is recrystallized from methanol/diethyl ether, yielding 680 mg of 2-(3,7-dihydroxy-1H-indazol-4-yl)ethylamine, hydrobromide, decomposition point 270°-273° C.

EXAMPLE 26

2-(3,7-Dihydroxy-1H-indazol-5-yl)ethylamine, Hydrobromide, and 2-(2,3-Dihydro-7-hydroxy-3-oxo-1H-indazol-5-yl)ethylamine, Hydrobromide Under argon, 450 mg of N-[2-(3-hydroxy-7-methoxy-1H-indazol-5-yl)ethyl]trifluoroacetamide in 10 ml of aqueous hydrogen bromide (65%) is heated to 120° C. for 3 hours. The precipitate is recrystallized from methanol/diethyl ether, thus obtaining 400 mg of 2-(2,7-dihydroxy-1H-indazol-5-yl)ethylamine, hydrobromide, decomposition point 253°–255° C.

EXAMPLE 27

N-[2-(3,7-Dihydroxy-1H-indazol-5-yl)ethyl]-N,N-dipropylamine, Hydrobromide, and N-[2-(2,3-Dihydro-7-hydroxy-3-oxo-1H-indazol-5-yl)ethyl]-N,N-dipropylamine, Hydrobromide N,N-Dipropyl-N-[2-(3-hydroxy-7-methoxy-1H-indazol-5-yl)ethyl]amine, hydrochloride, is reacted with hydrogen bromide as described in Example 24, thus producing N-[2-(3,7-dihydroxy-1H-indazol-5-yl)ethyl]-N,N-dipropylamine, hydrobromide.

EXAMPLE 28

N-[2-(7-Amino-1H-indazol-5-yl)ethyl]-N,N-dimethylamine, Dihydrochloride

N,N-Dimethyl-N-[2-(7-nitro-1H-indazol-5-yl)ethyl]amine is hydrogenated as described in Example 13 and treated with hydrochloric acid, thus forming N-[2-(7-amino-1H-indazol-5-yl)ethyl]-N,N-dimethylamine, dihydrochloride.

EXAMPLE 29

N,N-Dimethyl-N-[2-(7-hydroxy-1H-indazol-5-yl)ethyl]amine, Hydrochloride

As described in Example 14, N-[2-(7-amino-1H-indazol-5-yl)ethyl]-N,N-dimethylamine, dihydrochloride, is hydrolyzed with sulfuric acid, thus producing N,N-dimethyl-N-[2-(7-hydroxy-1H-indazol-5-yl)ethyl]amine, hydrochloride.

EXAMPLE 30

4-[2-(N,N-Dimethylamino)ethyl]benzimidazol-7-ol, Dihydrobromide (a) 0.30 g of N-[2-(2,3-diamino-4-methoxyphenyl)ethyl]-N,N-dimethylamine is heated under reflux for 3 hours with 10 ml of formic acid. The solution is filtered and concentrated, thus obtaining 0.23 g of 7-methoxy-4-[2-(N,N-dimethylamino)ethyl]benzimidazole, formate, as a vitreous mass.

(b) 225 mg of the compound obtained in (a) is heated under reflux with 5 ml of 48% strength hydrobromic acid for 3 hours. After concentration, the residue is recrystallized from an ethanol/diethyl ether mixture, yielding 260 mg of 4-[2-(N,N-dimethylamino)ethyl]benzimidazol-7-ol, dihydrobromide, mp 245°–252° C.

EXAMPLE 31

4-[2-(N,N-Dipropylamino)ethyl]benzimidazol-7-ol, Dihydrobromide (a) 1.2 g of N-[2-(2,3-diamino-4-methoxyphenyl)ethyl]-N,N-dipropylamine is heated under reflux with 20 ml of formic acid for 3 hours. The solution is concentrated. The residue is taken up in water, made alkaline with potassium carbonate, and extracted with ethyl acetate. The organic phase is dried over sodium sulfate and concentrated after the drying agent has been removed by filtration. The residue is chromatographed on silica gel with a mixture of dichloromethane/methanol, thus obtaining 0.42 g of 7-methoxy-4-[2-(N,N-dipropylamino)ethyl]benzimidazole as an oil.

(b) 0.42 g of the compound obtained in (a) is dissolved in 10 ml of dichloromethane. To the solution, cooled to 0° C., 2.0 g of boron tribromide is added dropwise. The reaction mixture is gradually warmed to room temperature. After 14 hours, the mixture is again cooled to 0° C., and 10 ml of methanol is added. The mixture is concentrated and the residue recrystallized from isopropanol/diethyl ether, thus obtaining 0.44 g of 4-[2-(N,N-dipropylamino)ethyl]benzimidazol-7-ol, dihydrobromide, mp 135°–139° C.

EXAMPLE 32

4-[2-(N,N-Dimethylamino)ethyl]-2-methylbenzimidazol-7-ol, Dihydrobromide (a) 0.6 g of N-[2-(2,3-diamino-4-methoxyphenyl)ethyl]-N,N-dimethylamine is heated under reflux with 10 ml of acetic acid for 3 hours. The reaction mixture is concentrated, taken up in ethyl acetate, and extracted by shaking with sodium bicarbonate solution. The organic phase is separated, dried with sodium sulfate, and concentrated, thus obtaining 286 mg of 7-methoxy-4-[2-(N,N-dimethylamino)ethyl]-2-methylbenzimidazole as an oil.

(b) 225 mg of the compound produced in (a) is heated under reflux for 3 hours with 5 ml of 48% strength hydrobromic acid. After concentration, the residue is recrystallized from an isopropanol/diethyl ether mixture, thus obtaining 178 mg of 4-[2-(N,N-dimethylamino)ethyl]-2-methylbenzimidazol-7-ol, dihydrobromide, having a melting point higher than 280° C.

EXAMPLE 33

2-Butyl-4-[2-(N,N-dimethylamino)ethyl]benzimidazol-7-ol, Dihydrobromide (a) 500 mg of N-[2-(2,3-diamino-4-methoxyphenyl)ethyl]-N,N-dimethylamine is heated with 10 ml of valeric acid for 7 hours to 120° C. The reaction mixture is concentrated. The residue is taken up in diethyl ether and extracted with 4N hydrochloric acid. The aqueous phase is neutralized with potassium bicarbonate solution and extracted with ethyl acetate. The organic phase is dried with sodium sulfate and concentrated, thus producing 170 mg of 2-butyl-7-methoxy-4-[2-(N,N-dimethylamino)ethyl]benzimidazole, mp 116°–122° C., after recrystallizing the residue from ethyl acetate.

(b) 130 mg of the compound obtained in (a) is heated under reflux with 3 ml of 48% strength hydrobromic acid for 4 hours. After concentration, the residue is recrystallized from an isopropanol/diethyl ether mixture, thus producing 108 mg of 2-butyl-4-[2-(N,N-dimethylamino)ethyl]benzimidazol-7-ol, dihydrobromide, mp 97°–105° C.

EXAMPLE 34

4-[2-(N,N-Dimethylamino)ethyl]-2-trifluoromethylbenzimidazol-7-ol, Hydrobromide (a) 600 mg of N-[2-(2,3-diamino-4-methoxyphenyl)ethyl]-N,N-dimethylamine is heated under reflux for 3 hours with 10 ml of trifluoroacetic acid. After concentration, the residue is recrystallized from isopropanol, thus obtaining 908 mg of 7-methoxy-4-[2-(N,N-dimethylamino)ethyl]-2-trifluoromethylbenzimidazole, trifluoroacetate, mp 182°–185° C.

(b) 400 mg of the compound obtained in (a) is heated under reflux for 3 hours with 3 ml of 48% strength hydrobromic acid. After concentration, the residue is recrystallized from butanol. Yield: 100 mg of 4-[2-(N,N-dimethylamino)ethyl]-2-trifluoromethylbenzimidazol-7-ol, hydrobromide, mp 198°–200° C.

EXAMPLE 35

7-Hydroxy-4-[2-(N,N-dimethylamin)ethyl]-2,3-dihydro-2-benzimidazolone, Hydrobromide (a) 500 mg of N-[2-(2,3-diamino-4-methoxyphenyl)ethyl]-N,N-dimethylamine is heated under reflux for 3 hours with 40 ml of tetrahydrofuran and 500 mg of N,N'-carbonyldiimidazole. After concentration, the residue is combined with methanol and water. The mixture is again concentrated and dried over phosphorus pentoxide, thus obtaining 410 mg of 7-methoxy-4-[2-(N,N-dimethylamino)ethyl]-2,3-dihydro-2-benzimidazolone, mp 197°–199° C.

(b) 200 mg of the compound obtained in (a) is heated under reflux for 2 hours with 10 ml of 48% strength hydrobromic acid. After concentration, the residue is recrystallized from an isopropanol/methanol/diethyl ether mixture, yielding 180 mg of 7-hydroxy-4-[2-(N,N-dimethylamino)ethyl]-2,3-dihydro-2-benzimidazolone, hydrobromide, mp 263°–269° C.

EXAMPLE 36

7-Hydroxy-4-[2-(N,N-dipropylamino)ethyl]-2,3-dihydro-2-benzimidazolone, Hydrobromide (a) 530 mg of N-[2-(2,3-diamino-4-methoxyphenyl)ethyl]-N,N-dipropylamine is heated under reflux for one hour with 30 ml of tetrahydrofuran and 500 mg of N,N'-carbonyldiimidazole. After concentration, the residue is combined with methanol and water, again concentrated, and dried over phosphorus pentoxide, yielding 530 mg of 7-methoxy-4-[2-(N,N-dipropylamino)ethyl]-2,3-dihydro-2-benzimidazolone, mp 35° C.

(b) 200 mg of the compound obtained in (a) is heated under reflux for 4 hours with 10 ml of 48% strength hydrobromic acid. After concentration, the residue is recrystallized from an isopropanol/diethyl ether mixture, thus producing 170 mg of 7-hydroxy-4-[2-(N,N-dipropylamino)ethyl]-2,3-dihydro-2-benzimidazolone, hydrobromide, mp 250°–255° C.

EXAMPLE 37

2-Amino-4-[2-(N,N-dimethylamino)ethyl]benzimidazol-7-ol, Dihydrobromide (a) 1.0 g of N-[2-(2,3-diamino-4-methoxyphenyl)ethyl]-N,N-dimethylamine is heated for 5 hours under reflux with 0.4 ml of concentrated hydrochloric acid, 217 mg of cyanamide, and 0.5 ml of water. Subsequently 0.5 ml of a 50% strength potassium hydroxide solution is added and the mixture again heated under reflux for 4 hours. Then the mixture is concentrated and the residue extracted with isopropanol. After adding hydrobromic acid, the thus-formed precipitate is recrystallized from ethanol, yielding 260 mg of 2-amino-7-methoxy-4-[2-(N,N-dimethylamino)ethyl]benzimidazole, dihydrobromide, decomposition point 260° C.

(b) 260 mg of the compound produced in (a) is heated under reflux for 2 hours with 5 ml of 63% strength hydrobromic acid. After concentration, the residue is recrystallized from ethanol, yielding 91 mg of 2-amino-4-[2-(N,N-dimethylamino)ethyl]benzimidazol-7-ol, dihydrobromide, with a decomposition point of 250° C.

EXAMPLE 38

4-[2-(N,N-Dimethylamino)ethyl]benzotriazol-7-ol, Dihydrobromide (a) 1.0 g of N-[2-(2,3-diamino-4-methylphenyl)ethyl]-N,N-dimethylamine is dissolved in 1.2 ml of acetic acid and 2.4 ml of water. To this mixture is added dropwise a solution of 425 mg of sodium nitrite in 0.7 ml of water. After 20 minutes the mixture is neutralized with 2N ammonia solution and concentrated. The residue is combined with hydrobromic acid and recrystallized from methanol, thus obtaining 1.0 g of 7-methoxy-4-[2-(N,N-dimethylamino)ethyl]benzotriazole, hydrobromide, mp 176°–180° C.

(b) 1.0 g of the compound obtained in (a) is heated under reflux for 5 hours with 20 ml of 48% strength hydrobromic acid. After concentration, the residue is recrystallized from isopropanol, thus producing 220 mg of 4-[2-(N,N-dimethylamino)ethyl]benzotriazol-7-ol, dihydrobromide, mp 207°–211° C.

EXAMPLE 39

7-Hydroxy-4-[2-(N,N-dimethylamino)ethyl]-2,3-dihydro-2-benzimidazolethione, Hydrobromide (a) 500 mg of N-[2-(2,3-diamino-4-methoxyphenyl)ethyl]-N,N-dimethylamine is heated for 3 hours under reflux with 50 ml of tetrahydrofuran and 430 mg of N,N'-thiocarbonyldiimidazole. After concentration, the residue is combined with water. The precipitate is recrystallized from ethanol, thus obtaining 470 mg of 7-methoxy-4-[2-(N,N-dimethylamino)ethyl]-2,3-dihydro-2-benzimidazolethione, mp 213°–216° C.

(b) 200 mg of the compound obtained in (a) is heated under reflux for 2 hours with 5 ml of 63% strength hydrobromic acid. After concentration, the residue is recrystallized from an isopropanol/diethyl ether mixture, yielding 85 mg of 7-hydroxy-4-[2-(N,N-dimethylamino)ethyl]-2,3-dihydro-2-benzimidazolethione, hydrobromide, decomposition point 210° C.

EXAMPLE 40

7-Hydroxy-4-(2-aminoethyl)-2,3-dihydro-2-benzimidazolone, Hydrobromide (a) 1.9 g of 4-methoxy-2,3-dihydro-2bvenzimidazolone (DOS 2,819,458 of Nov. 16, 1978) is maintained in an ultrasonic bath for 4 hours with 40 ml of methylene chloride, 6.0 g of tin tetrachloride, and 2.7 g of dichloromethyl methyl ether (heat buildup). The mixture is extensively concentrated and the residue combined with water. After filtering off and drying, 1.8 g of 7-methoxy-2,3-dihydro-2-benzimidazolone-4-aldehyde is obtained, mp 256°–262° C.

(b) 1.8 g of the compound obtained in (a) is reacted with 0.7 g of nitromethane, 50 ml of methanol, and 0.6 g of sodium hydroxide in 10 ml of water. After 30 minutes the mixture is poured on ice-cold, semiconcentrated hydrochloric acid and the precipitate is filtered off. After recrystallization from ethanol, 1.2 g of 7-methoxy-4-(2-nitrovinyl)-2,3-dihydro-2-benzimidazolone is produced, having a decomposition point of 250° C.

(c) 1.2 g of the compound obtained in (b) is combined with 100 ml of methanol, 100 ml of water, 10 ml of 48% strength hydrobromic acid, and 400 mg of palladium-active carbon and hydrogenated at 50° C. After hydrogen absorption has ceased, the mixture is filtered off from the catalyst and, after concentration, 1.2 g of 7-methoxy-4-(2-aminoethyl)-2,3-dihydro-2-benzimidazolone, hydrobromide, is obtained, mp 180°-190° C.

(d) Cleavage of the methoxy compound is performed analogously to Example 6(b), thus obtaining 7-hydroxy-4-(2-aminoethyl)-2,3-dihydro-2-benzimidazolone, hydrobromide.

EXAMPLE 41

7-Hydroxy-4-[2-(N-butyl-N-propylamino)ethyl]-2,3-dihydro-2-benzimidazolone, Hydrobromide The compound according to Example 11(c) was acylated with propionyl chloride, then reduced with borane in tetra hydrofuran, the product reacylated with butyryl chloride, and reduced with borane in tetrahydrofuran. The thus-formed compound is then subjected to ether cleavage with hydrobromic acid, yielding 7-hydroxy-4-[2-(N-butyl-N-propylamino)ethyl]-2,3-dihydro-2-benzimidazolone, hydrobromide.

EXAMPLE 42

7-Hydroxy-4-[2-(N,N-dimethylamino)ethyl-]2,1,3-benzothiadiazole-2,2-dioxide, Hydrobromide (a) 2.0 g of N-[2,3-diamino-4-methoxyphenyl)ethyl]-N,N-dimethylamine is dissolved in 17 ml of diglyme and heated under reflux. A solution of 1.12 g of sulfamide in 5 ml of diglyme is added to the boiling mixture. After 10 minutes, the mixture is quickly cooled down. The precipitate is filtered off and recrystallized from ethanol, thus obtaining 1.12 g of 7-methoxy-4-[2-(N,N-dimethylamino)ethyl]-2,1,3-benzothiadiazole-2,2-dioxide, mp 202°-207° C.

(b) 500 mg of the compound produced in (a) is mixed with 20 ml of a 1-molar boron tribromide solution in dichloromethane. After 48 hours, methanol is added and the reaction mixture concentrated to dryness. The residue is recrystallized from ethanol, thus obtaining 332 mg of 7-hydroxy-4-[2-(N,N-dimethylamino)ethyl]-2,1,3-benzothiadiazole-2,2-dioxide, hydrobromide, mp 202°-205° C.

We claim:
1. A dopamine derivative of Formula

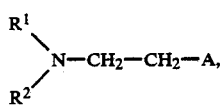

wherein
A is

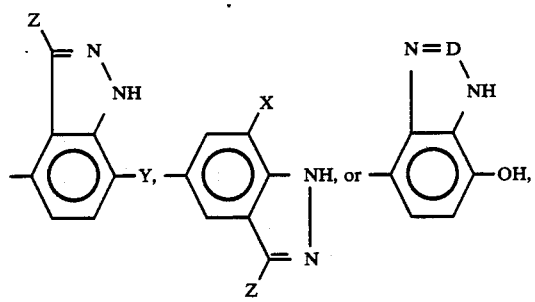

wherein
R$^1$ and R$^2$ are identical or different, and each is hydrogen, C$_{1-5}$-alkyl or allyl,
D is

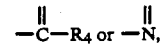

R$_4$ is hydrogen, C$_{1-4}$-alkyl, CF$_3$, or NH$_2$,
X is NH$_2$,

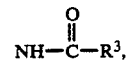

or NH—SO$_2$—CF$_3$, and Y=OH,
Y is NH$_2$,

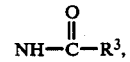

NH-SO$_2$—CF$_3$ or NH-SO$_2$—CH$_3$, and X=OH, and one of X and Y is always OH, except with the proviso that X and Y are not simultaneously OH and NH—SO$_2$—CH$_3$, and vice versa, with R$^3$ being hydrogen or C$_{1-4}$-alkyl, and
Z is H or OH, and, when Z is hydroxy, the residue A can also be in the tautomeric basic form,
or an acid addition salt thereof.

2. N,N-Dipropyl-N-[2-(7-amino-1H-indazol-4-yl)ethyl]amine and its dihydrochloride, a compound of claim 1.

3. A dopamine derivative of claim 1, wherein A is

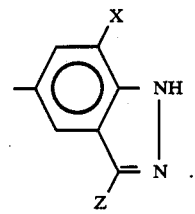

4. A dopamine derivative of claim 1, wherein A is

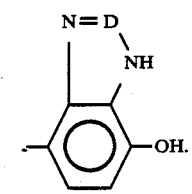

5. A dopamine derivative of claim 1, wherein A is

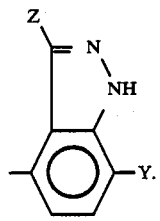

* * * * *